United States Patent [19]

Fortunak

[11] Patent Number: 4,997,954

[45] Date of Patent: Mar. 5, 1991

[54] PROCESS FOR PREPARING SUBSTITUTED ISOINDOLINONE DERIVATIVES

[75] Inventor: Joseph M. Fortunak, Strafford, Pa.

[73] Assignee: Smith Kline & French Laboratories Limited, Welwyn Garden City, Great Britain

[21] Appl. No.: 207,351

[22] Filed: Jun. 15, 1988

[30] Foreign Application Priority Data

Jun. 19, 1987 [GB] United Kingdom ................ 8714371

[51] Int. Cl.$^5$ .......................................... C07D 209/40
[52] U.S. Cl. .................................................. 548/486
[58] Field of Search ....................................... 548/486

[56] References Cited

U.S. PATENT DOCUMENTS 4,588,740 5/1986 Gallagher, Jr. ..................... 548/486
4,761,485 8/1988 Marfat ................................. 548/486

FOREIGN PATENT DOCUMENTS 0113964 7/1984 European Pat. Off. .

OTHER PUBLICATIONS

Guillanmel, J. et al. (1980), Heterocycles, 17, pp. 1531–1536.

J. Guillaumel et al., Tetrahedron, vol. 36, pp. 2459–2465 (1980).

R. Morrison et al., Organic Chemistry, Second edition, p. 735 (1967), Allyn and Bacon, Inc., Boston.

Primary Examiner—Mary E. Ceperley
Attorney, Agent, or Firm—Wayne J. Dustman; Stuart R. Suter; Edward T. Lentz

[57] ABSTRACT

This invention relates to an improved process for the preparation of substituted indolinone derivatives using reductive cyclization conditions.

8 Claims, No Drawings

PROCESS FOR PREPARING SUBSTITUTED ISOINDOLINONE DERIVATIVES

PROCESS

The present invention relates to an improved process for the preparation of substituted indolinone derivatives. Such compounds are described in EP 113964 as being useful in cardiovascular therapy.

Processes for the preparation of substituted indolinone derivatives have previously been described, in particular those involving reductive cyclisation of nitrostyrene compounds in the presence of acetyl chloride and iron (III) chloride, see for example, Guillanmel, J. et al. (1980) Tetrahedron 36 p.2459–2465 and Guillanmel, J. et al. (1980) Heterocycles 17 p.153–1536. The shortcoming of these teachings is the low yields of the cyclised product and the generation of a mixture of other uncyclised products. In only one example in these references is there formation of a single cyclised product with a yield of only 49%.

It has now been found that certain substituted indolinones can be prepared under reductive cyclisation conditions in significantly higher yields (up to 98% of essentially only the cyclised product) than would have been expected from the aforementioned teachings.

The present invention therefore provides a process for the preparation of a compound of structure (I)

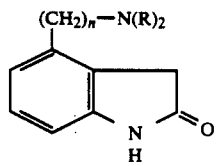

in which each group R is hydrogen, $C_{1-6}$alkyl, $C_{3-6}$allyl, Phenyl$C_{1-6}$alkyl or 4-hydroxyphenyl $C_{1-6}$alkyl, and n is 1 to 3 or a pharmaceutically acceptable salt thereof, which comprises reductive cyclisation of a compound of structure (II).

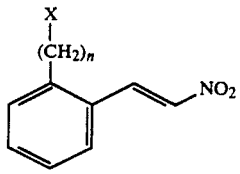

in which X is a group displaceable by amine, in the presence of at least two equivalents of anhydrous iron (III) chloride and at least two equivalents of an acetyl halide and a solvent to form a compound of structure (III)

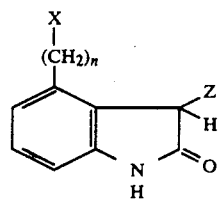

in which X and n are as hereinabove defined, Z is halogen followed by subsequent dehalogenation of the compound of structure (III) to form a compound of structure (IV)

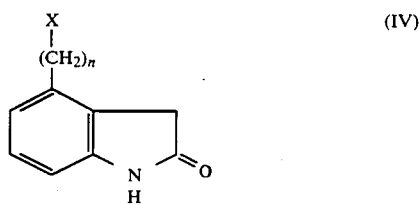

in which X and n are as hereinabove defined and thereafter
replacing the group X with a group $N(R)_2$ wherein R is as hereinabove defined, and
optionally forming a pharmaceutically acceptable salt.

Suitably the acetyl halide used in the cyclisation of a compound of the structure (II) is acetyl bromide. Preferably the acetyl halide is acetyl chloride.

Suitably, the solvent used in the cyclisation of a compound of the structure (11) is a chlorinated hydrocarbon for example dichloromethane or 1,2-dichloroethane. Preferably the solvent is dichloromethane.

Suitably, X is halogen; preferably bromine.
Suitably, Z is bromine; preferably chlorine.
Suitably, n is 1 or 3, preferably n is 2. Suitably each group R is $C_{1-4}$alkyl, preferably propyl. Suitably, the cyclisation of the compound of structure II is carried out in the presence of two equivalents of acetyl chloride or acetyl bromide and two equivalents of iron (III) chloride. Preferably the cyclisation is carried out in the presence of two equivalents of acetyl chloride and three equivalents of iron (III) chloride.

Preferably, therefore, the process of the present invention is particularly useful for preparing compounds of structure (IIIA)

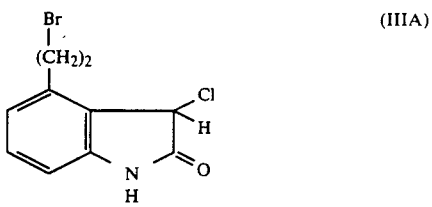

and converting them into the following compound of structure (I)

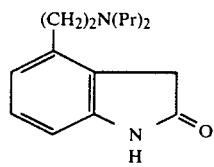

or the hydrochloride salt thereof.

The starting nitrostyrene compounds of structure (II) can be prepared by processes well known to those skilled in the art. For example, treatment of isochroman (commercially available e.g. from The Aldrich Chemical Company) with bromine gives the corresponding 2-(2'-bromoethyl)benzaldehyde which on reaction with nitromethane in the presence of, for example sodium methoxide, gives the desired nitrostyrene compound i.e.

(2′-bromoethyl)-β-nitrostyrene. The invention is illustrated by the following

EXAMPLE 1

Preparation and purification of 2(2′-bromoethyl)benzaldehyde

Bromine (29.6 g, 185.2 mmols) in dichloromethane (20 ml) was added to isochroman (25 g. 186.0 mmol) in dichloromethane (150 ml) over one hour in the presence of a strong light source at such a rate that the reaction temperature was about 35° C. The mixture was left for a further hour in the presence of the light source, keeping the temperature of the mixture below 40° C. The mixture was concentrated under reduced pressure to give a heavy yellow oil. This was then left on an oil bath at 80° C. under nitrogen for one and a half hours. The crude product was dissolved in dichloromethane (150 ml). Washed with water (100 ml). Saturated sodium bicarbonate (30 ml) was made up to 100 ml with water and this was used to wash the organic layer. This layer was again washed with water and then dried ($Mg_2SO_4$). Excess solvent was removed under reduced pressure to give a heavy yellow oil of 2(2′-bromoethyl)benzaldehyde 34.07 g (88 9%).

Purification

Sodium metabisulphite (25 g) was dissolved in water (25 ml) and to this was added industrial methylated spirit (20 ml). The benzaldehyde above was added and stirred for 30 minutes after which dichloromethane (75 ml) was added. The resulting suspension was filtered to give a white powder. To a sodium carbonate solution (13.5 g in water (220 ml)) the solid was added and to this mixture was added dichloromethane (50 ml). After shaking the organic layer and aqueous layers were separated. The extractions were repeated twice. The resultant three extracts were combined, dried ($Mg_2SO_4$) and then concentrated to give 14.99 g of a clear pale yellow oil, of 2(2′-bromoethyl)-benzaldehyde yield 43.9% b.p.110° C./0.04 mm Hg 5.33 $Nm^{-2}$.

EXAMPLE 2A

Preparation of 2-(2′-bromoethyl)B-nitrostyrene

Nitromethane (47.9 q 0.785 moles) was dissolved in methanol (250 ml) under nitrogen and the solution was cooled to −10° C. Sodium methoxide solution (29.6%. 106.7 g) in methanol (70 ml) was added over 50 minutes at −10° C. and the resulting suspension stirred for a further 50 minutes at −30° to −35° C. 2-(2′-bromoethyl)benzaldehyde (106.5 g. 0.5 moles) in dimethylformamide (220 ml) was added over 30 minutes at −35° C. The mixture was stirred a further 40 minutes at −30° C. and then quenched into hydrochloric acid (1100 ml. 6N) at 0° C. The resulting yellow solid was filtered off, washed with water and dried to give 102.0 g (70%) of 2-(2′-bromoethyl)8-nitrostyrene, m.p. 67°–68° C.

EXAMPLE 2B

Preparation of 2-(2′-bromoethyl)-8-nitrostyrene 2-(2′-Bromoethyl)benzaldehyde (10 g) was added to methanol (200 ml) which had already been basified with a small amount of sodium methoxide solution (1 g. 30% weight/weight in methanol). Nitromethane (3.7 g) was then added and the resultant solution was cooled to about 0° C. under nitrogen. A 30% solution of sodium methoxide (9 g) in methanol (50 ml) was then added with stirring over about 30 minutes. The reaction mixture was then stirred at about 0° C. for 1 hour before being pumped into 6N hydrochloric acid (200 ml). 2-(2′-bromoethyl)-β-nitrostyrene (9.51 g. 80%) precipitated as a yellow crystalline solid which was collected by filtration and air dried at 20°–30° C.

Pre-basification of methanol allows the use of a single solvent, safer mode of addition and more easily obtained reaction temperature.

EXAMPLE 3A

Preparation of 4-(2′-bromoethyl)-3-chloro-1,3-dihydro-2H-indol-2-one

A solution of 2-(2′-bromo)-β-nitrostyrene (1.69 g. 6.6 mmol) in dichloromethane (50 ml) was cooled with stirring to 0° C. To this solution was added acetyl chloride (0.96 ml. 1.06 g. 13.5 mmol). followed by powdered anhydrous ferric chloride (4.38 g. 27 mmol). The dark red suspension was stirred rapidly at 0° C. for 5.5 hours. After pouring into 100 ml each of 5% hydrochloric acid and chloroform and shaking for 5 minutes the layers were separated. Drying over $MgSO_4$ was followed by evaporation of the chloroform layer to give 1.78 g (98%) of 4-(2′-bromoethyl)-3-chloro-1,3-dihydro-2H-indol-2-one as an off-white, crystalline powder. Trituration with ether or recrystallization from 15/1 chloroform/ethanol yielded a white powder. The crude product can be directly dechlorinated without purification.

EXAMPLE 3B

Preparation of 4-(2′-bromoethyl)-3-chloro-1,3-dihydro-2H-indol-2-one

To a solution of 2(2′-bromoethyl)-β-nitrostyrene (44 g, 172 mmol) in dichloromethane (1000 ml) at −10° C. was added, in quick succession, acetyl chloride (24 ml, 338 mmol) and ferric chloride (83.8 g, 516 mmol). The reaction mixture was stirred at −10° C. to 0° C. for five hours before washing with aqueous 1N solutions of hydrochloric acid (2×750 ml). After drying, the dichloromethane was removed in vaccuo leaving a sticky brown solid (57 g) which was slurried in dichloromethane/ petrol [40°–60° C. (3:1, 10 volumes)]. The resulting light brown solid was collected to give 30.76 g. (65%) of 4-(2′-bromoethyl)-3-chloro-1.3-dihydro-2H-indol-2-one m.p. 168°–170° C.

Large scale preparations of 4-(2′-bromoethyl)-3-chloro-1.3-dihydro-2H-indol-2-one were also prepared as set out in examples 3C, 3D and 3E below.

EXAMPLE 3C

Preparation of 4-(2′-bromoethyl)-3-chloro-1,3-dihydro-2H-indol-2-one

To a precooled solution of ferric chloride (28.5 kg) in dichloromethane (340 l) at 0° C. was added acetyl chloride (9.2 kg) at such a rate that the reaction temperature did not exceed 5° C. The reaction mixture was stirred at between 0° and 5° C. for 15 minutes. To the mixture was added a pre-dryed solution of 2-(2′-bromoethyl)-β-nitrostyrene [12.88 kg (16.22 kg wet:water content 20.6%)]in dichloromethane (55 litres) at such a rate that the reaction temperature did not exceed 5° C. The reaction mixture was stirred for 5 hours at a temperature between 5 and 10° C. Analysis by TLC confirmed that the reaction had gone to completion. Water (240 l) was then added to the reaction mixture at such a rate so that the temperature did not exceed 20° C. The mixture was then stirred for 30 minutes. The dichloromethane layer was isolated and washed a further three times with water (three times 120 l). The dichloromethane layer was then distilled to a volume of about 60 l. After cooling to 20° C. petroleum ether (60/80 grade, 40 l) was added and the resulting precipitate was stirred at 10° C. for 30 minutes. HPLC analysis of the crude reaction mixture indicated a purity of 93.22% of the required product. 4-(2'-bromo-ethyl)-3-chloro-1,3-dihydro-2H-indol-2-on by filtration, the filtrate washed with petroleum ether (60 l) and dried at 80° C. overnight to give 10.8 kg (78%) of of the title compound.

EXAMPLE 3D

Preparation of 4-(2'-bromoethvl)-3-chloro-1,3-dihydro-2H-indol-2-one

The procedure of Example 3C was carried out except that the amount of 2-(2'-bromoethyl)-β-nitrostyrene was 2.88 kg (16.95 kg wet:water content 24%). HPLC analysis of the crude reaction mixture indicated a purity of 96.83% of the required product. Isolation of the product gave 7.5 kg (54%) of the title compound.

EXAMPLE 3E

Preparation of 4-(2'-bromoethyl)-3-chloro-1,3-dihydro-2H-indol-2-one

The procedure of Example 3C was carried out except that the amount of 2-(2'-bromoethyl)-β-nitrostyrene was 1.7 kg (15.28 kg wet:water content 23.4%). HpLC analysis of the crude reaction mixture indicated a purity of 96.2% of the required product. Isolation of the product gave 5.7 kg (54%) of the title compound.

EXAMPLE 4A Preparation of 4-(2'-bromoethyl)-1,3-dihydro-2H-indol-2-one 4-(2'-Bromoethyl)-3-chloro-1.3-dihydro-2H-indol-2-one (34.5 g. 126 mmol) was stirred together with 10% palladium/ carbon (3.5 g) and sodium hypophosphite hydrate (45 g) in 99% industrial methylated spirit/water 19:1 mixture (400 ml) was added at 85° C. The reaction was completed within one hour as monitored by HPLC. The reaction was filtered and concentrated in vaccuo to leave a yellow solid which was then stirred as a slurry in water/industrial methylated spirit [9:1 (200 ml)]filtered and dried overnight to give 26.32 g. (87%) of 4-(2'-bromoethyl)-1.3-dihydro-2H-indol2-one m.p. 140–145° C. An HPLC profile showed this product to be essentially one component (92.8% purity).

EXAMPLE 4B

Preparation of 4-(2'-bromoethyl)-1.3-dihydro-2H-indol-2-one 4-(2'-Bromoethyl)-3-chloro-1,3-dihydro-2H-indol-2-one (23.6 g. 86 mmol), sodium hypophosphite hydrate (35 g) and 10% palladium/carbon (60% w/w wet, 2.6 g) were stirred in industrial methylated spirit (250 ml)/water (30 ml) at 80° C. The reaction was complete after 2 hours as monitored by HPLC. Inorganic components were removed by filtration and the organic solvent was removed in vaccuo. The solid residue was slurried in water (100 ml) and dried overnight to give 17.0 g (82%) of 4-(2'-bromoethyl)-1,3-dihydro-2H-indol-2-one.

EXAMPLE 4C

Preparation of 4-(2'-bromoethyl1)1,3-dihydro-2H-indol-2-one

To a stirred suspension of 10% palladium/carbon (0.5 g, 0.2 mmol) 4-(2'-bromoethyl)-3-chloro-1.3-dihydro2H-indol-2-one (5 g, 18.2 mmol), in ethyl acetate (100 ml). heated under reflux, was added aqueous sodium hypophosphite in water (5 g in 30 ml, 47.2 mmoles) over a 15 minute period. Thin layer chromatography (methanol: CH$_2$Cl$_2$, 1:30) immediately after addition showed that the reaction was complete. The reaction mixture was filtered hot through a hi-flow bed and the water layer was removed before the filtrate was concentrated totally in vacuo. The solid residue was stirred as a slurry in water (120 ml) and collected at the pump. The amount of white solid (4-(2'-bromoethyl)1,3-dihydro-2H-indol-2-one) obtained was 4.16 g (95%). purity assessed by HPLC for 4(-2'-bromoethyl)1,3-dihydro-2H-indol-2-one was 99.11%.

EXAMPLE 5A

Preparation of 4-2-(Dipropylamino)ethyl}-1,3-dihydro-2H-indol-2-one

Under an atmosphere of nitrogen, a suspension of 4-(2'-bromoethyl)-1,3-dihydro-2H-indol-2-one (245 mg, 102 mmol) was prepared by the addition of di-n-propylamine (1.00 g, 10 mmol, 1.35 ml) which has previously been degassed with a stream of nitrogen. After stirring for 30 minutes, degassed acetonitrile (5 ml) was added to give a pale yellow solution. After an additional hour the solution was heated, and maintained at reflux for 5 hours. After cooling to ambient temperature, the solution was poured into IN hydrochloric acid (35 ml) and extracted with ether (50 ml). The aqueous layer was made neutral to pH 7–7.5 with solid sodium bicarbonate and extracted with dichloromethane (50 ml). After drying separately, the ether layer was evaporated to give 4-vinyl-indol-2-one (60 mg, 37.7%) Evaporation of the dichloromethane layer gave 4-[2-(dipropylamino)ethyl]-1.3-dihydro-2H-indol-2-one (155 mg. 58.5%) as free-base which was then taken up in absolute ethanol (5 ml) and saturated with gaseous hydrogen chloride. The solvent was removed in vaccuo to give the crude hydrochloride salt (170 mg) as a light yellow solid. Recrystallisation from absolute ethanol (2 ml) gave light yellow crystals (110 mg 63% from the free-base) of 4-[2-(dipropylamino)ethyl]-1,3- dihydro-2H-indol-2-one hydrochloride m.p. 242–244° C.

EXAMPLE 5B

Preparation of 4-[2-(Dipropylamino)ethyl)-1,3-dihydro-2H-indol-2-one (hydrochloride)

Water (200 ml) was heated under reflux in an atmosphere of nitrogen, and then cooled to room temperature. 4-(2'-Bromoethyl)-1,3-dihydro-2H-indol-2-one (10 g) and di-n-propylamine (42 g) were added to the water, stirred vigorously, and heated to 90–93° C. for a period of 90 minutes. HPLC indicated that all the starting material had been consumed. Excess di-n-propylamine was removed by vacuum azeotropic distillation, and the reaction mixture was then stirred at about 30° C. The reaction mixture was extracted with ethyl acetate (60 ml). and the organic layer was then removed, dried (MgSO$_4$). filtered, and then diluted with isopropanol (100 ml). The ethyl acetate/ isopropanol solution was stirred at 0° C., and concentrated hydrochloric acid (3 ml) was added. A yellow precipitate was formed, which was collected at the pump, washed with isopropanol (50 ml) and then dried at 80° C. overnight under Nash Vacuum. This gave a yellow powder which was 4-[2-(dipropylamino)ethyl]-1,3-dihydro-2H-indol-2-one hydrochloride (6.6g 53% yield). purity by HpLC was 97.00%.

Typically, batches of this material were further purified by either recrystallisation from isopropanol, or basification and re-acidification procedures to give a product of 98-99% purity.

What is claimed is:

1. A process for the preparation of a compound of structure (I)

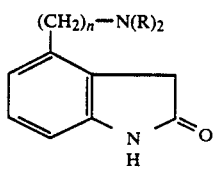

in which n is 1 to 3; and each group R is hydrogen, $C_{1-6}$alkyl, $C_{3-6}$allyl, phenyl $C_{1-6}$alkyl or 4-hydroxyphenyl $C_{1-6}$alkyl, or a pharmaceutically acceptable salt thereof, which comprises reductive cyclisation of a compound of structure (II)

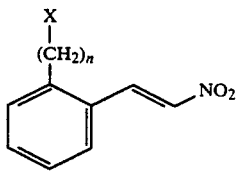

in which X is a group displaceable by amine in the presence of at least two equivalents of anhydrous iron (III) chloride and at least two equivalents of an acetyl halide and a solvent to form a compound of structure (III)

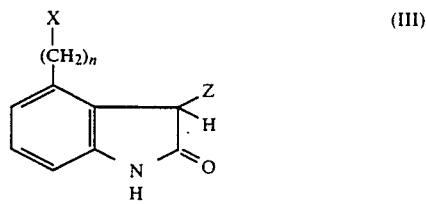

in which X and n are as hereinabove defined, Z is halogen followed by dehalogenation of a compound of structure (III) to form a compound of structure (IV)

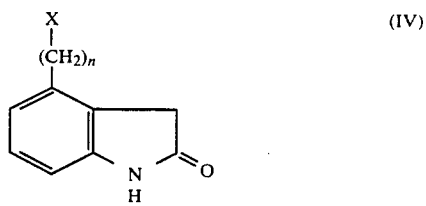

in which X and n are as hereinabove defined and thereafter replacing the group X with a group $N(R)_2$ wherein R is as hereinabove defined and optionally forming a pharmaceutically acceptable salt.

2. A process according to claim 1 in which the acetyl halide is acetyl bromide.

3. A process according to claim 1 in which the acetyl halide is acetyl chloride.

4. A process according to claim 3 in which the number of equivalents of acetyl chloride is 2 and the number of equivalents of iron (III) chloride is 3.

5. A process according to any one of claims 1 to 4 in which X is halogen.

6. A process according to claim 5 in which X is bromine.

7. A process for preparation of a compound of structure (III) as defined in claim 1 which comprises reductive cyclisation of a compound of structure (II) as defined in claim 1, in the presence of at least two equivalents of anhydrous iron (III) chloride, at least two equivalents of acetyl chloride and a solvent.

8. A process according to claim 7 in which the number of equivalents of acetyl chloride is 2 and the number of equivalents of iron (III) chloride is 3.

* * * * *

UNITED STATES PATENT AND TRADEMARK OFFICE
CERTIFICATE OF CORRECTION

PATENT NO. : 4,997,954
DATED : March 5, 1991
INVENTOR(S) : Fortunak

It is certified that error appears in the above-identified patent and that said Letters Patent is hereby corrected as shown below:

In column 3, line 1; change "(2'-bromoethyl)-ß-nitrostyrene." to -- 2-(2'-bromoethyl)-ß-nitrostyrene.--.

In column 3, line 57; change "2-(2'-bromoethyl)8-nitrostyrene" to -- 2-(2'-bromoethyl)-ß-nitrostyrene --.

In column 3, line 59; change "2-(2'-bromoethyl)-8-nitrostyrene" to -- 2-(2'-bromoethyl)-ß-nitrostyrene --.

In column 5, line 8; change "indol-2-on by filtration" to -- indol-2-one was collected by filtration --.

In column 5, line 17, change "2.88 kg" to -- 12.88 kg --.

In column 5, line 28; change "1.7 kg" to -- 11.7 kg --.

In column 6, line 19; change "4-2-(Dipropylamino)ethyl}-1," to -- 4-[2-(Dipropylamino)ethyl]-1, --.

UNITED STATES PATENT AND TRADEMARK OFFICE
CERTIFICATE OF CORRECTION

PATENT NO. : 4,997,954

DATED : March 5, 1991

INVENTOR(S) : Fortunak

It is certified that error appears in the above-identified patent and that said Letters Patent is hereby corrected as shown below:

In column 6, line 29; change "IN" to --1N--.

Signed and Sealed this

Third Day of November, 1992

Attest:

DOUGLAS B. COMER

Attesting Officer

Acting Commissioner of Patents and Trademarks